US010362966B2

(12) United States Patent
Kruger et al.

(10) Patent No.: US 10,362,966 B2
(45) Date of Patent: Jul. 30, 2019

(54) INTRAOPERATIVE IMAGE REGISTRATION BY MEANS OF REFERENCE MARKERS

(71) Applicant: Fiagon GmbH, Hennigsdorf (DE)

(72) Inventors: Timo Kruger, Berlin (DE); Dirk Mucha, Berlin (DE)

(73) Assignee: Fiagon GmbH, Hennigsdorf (DE)

( * ) Notice: Subject to any disclaimer, the term of this patent is extended or adjusted under 35 U.S.C. 154(b) by 41 days.

(21) Appl. No.: 14/890,480

(22) PCT Filed: May 16, 2014

(86) PCT No.: PCT/EP2014/060172
§ 371 (c)(1),
(2) Date: Nov. 11, 2015

(87) PCT Pub. No.: WO2014/184382
PCT Pub. Date: Nov. 20, 2014

(65) Prior Publication Data
US 2016/0106338 A1 Apr. 21, 2016

(30) Foreign Application Priority Data

May 16, 2013 (DE) .......................... 10 2013 209 158

(51) Int. Cl.
*A61B 5/06* (2006.01)
*A61B 6/00* (2006.01)
(Continued)

(52) U.S. Cl.
CPC .............. *A61B 5/066* (2013.01); *A61B 6/487* (2013.01); *A61B 6/5235* (2013.01); *A61B 6/547* (2013.01);
(Continued)

(58) Field of Classification Search
CPC ...................................................... A61B 5/066
(Continued)

(56) References Cited

U.S. PATENT DOCUMENTS 6,301,495 B1 * 10/2001 Gueziec ................. A61B 6/00
                                                    600/407
2001/0021806 A1 * 9/2001 Gueziec ............... A61B 6/032
                                                    600/425
(Continued)

FOREIGN PATENT DOCUMENTS

CN   101084840 A   12/2007
CN   102056544 A   5/2011
(Continued)

OTHER PUBLICATIONS

Maurer, C.R. et al. "Registration of Head Volume Images Using Implantable Fiducial Markers". IEEE Transactions on Medical Imaging 16.4 (1997): 447-462.*
(Continued)

*Primary Examiner* — Shivang I Patel
(74) *Attorney, Agent, or Firm* — Ware, Fressola, Maguire & Barber LLP (57) ABSTRACT

A method for incorporating tomographically obtained image data from a patient into a system for surgical planning and/or intraoperative navigation involves tomographic image data or image data obtained by X-ray recordings from at least one defined body area of the patient by at least one first recording appliance, wherein a first reference body having at least one surface is arranged on the patient and is recorded by the first recording appliance at the same time. The recorded image data representing the first reference body are compared with known geometric data from the first reference body in order to obtain distortion information. The recorded image data are equalized by a computation unit based on the distortion information to obtain equalized image data which have further image data from the same body area superimposed to obtain superimposed image data that is presented on a display.

18 Claims, 11 Drawing Sheets

(51) Int. Cl.
  *G06T 7/73* (2017.01)
  *A61B 17/00* (2006.01)
  *A61B 34/10* (2016.01)
  *A61B 34/20* (2016.01)
  *A61B 5/055* (2006.01)
  *A61B 90/00* (2016.01)
  *G06T 11/00* (2006.01)

(52) U.S. Cl.
  CPC .............. *A61B 6/584* (2013.01); *A61B 6/589* (2013.01); *A61B 90/39* (2016.02); *G06T 7/75* (2017.01); *G06T 11/00* (2013.01); *A61B 5/055* (2013.01); *A61B 2017/0092* (2013.01); *A61B 2034/107* (2016.02); *A61B 2034/2051* (2016.02); *A61B 2034/2065* (2016.02); *A61B 2090/364* (2016.02); *A61B 2090/3762* (2016.02); *A61B 2090/3966* (2016.02); *A61B 2090/3983* (2016.02); *A61B 2560/0228* (2013.01); *A61B 2576/00* (2013.01); *G06T 2200/04* (2013.01); *G06T 2207/10072* (2013.01); *G06T 2207/10121* (2013.01); *G06T 2207/20221* (2013.01); *G06T 2207/30012* (2013.01); *G06T 2207/30204* (2013.01)

(58) Field of Classification Search
  USPC ........................................................ 345/633
  See application file for complete search history.

(56) References Cited

U.S. PATENT DOCUMENTS

| | | | |
|---|---|---|---|
| 2008/0262345 A1 | 10/2008 | Fichtinger et al. | |
| 2009/0068620 A1 | 3/2009 | Knobel et al. | |
| 2011/0060213 A1 | 3/2011 | Mire et al. | |
| 2012/0143050 A1* | 6/2012 | Heigl .................... | A61B 90/39 600/424 |

FOREIGN PATENT DOCUMENTS

| | | |
|---|---|---|
| CN | 102917647 A | 2/2013 |
| DE | 19944981 A1 | 4/2001 |
| EP | 1278458 B1 | 1/2003 |

OTHER PUBLICATIONS

Maintz, JBA, et al.; "A Survey of Medical Image Registration"; Medical Image Analysis, Oxford University Press, Oxford, GB; Bd. 2, nr. 1; Jan. 1, 1998; whole document.

Maurer, Calvin R. Jr., et al; "Registration of Head Volume Images Using Implantable Fiducial Markers;" IEEE Transactions on Medical Imaging, IEEE Service Center, Piscataway, NJ; Bd. 16, Nr. 4; Aug. 1, 1997; pp. 447-460.

H. Dang, et al; "Robust methods for automatic image-to-world registration in cone-beam CT interventional guidance"; Medical Physics, AIP; vol. 39, No. 10; Oct. 2012; pp. 6484-6498.

* cited by examiner

INTRAOPERATIVE IMAGE REGISTRATION BY MEANS OF REFERENCE MARKERS

CROSS REFERENCE TO RELATED APPLICATIONS

This application is the U.S. National Stage of International Application Number PCT/EP2014/060172 filed on May 16, 2014 which application claims priority under 35 USC § 119 to German Patent Application No. 10 2013 209 158.3 filed on May 16, 2013, which applications are hereby incorporated by reference in their entirety.

TECHNICAL FIELD

The invention relates to a method for including image data obtained by means of an imaging method, in particular a tomographic method, in a system for operation planning and/or for intraoperative navigation, wherein the image data is initially obtained, or was obtained previously, by means of imaging methods such as x-ray and/or computed tomography. The invention also relates to a reference body, an electromagnetic field generator and a medical system, in particular for use in such a method in each case.

BACKGROUND OF THE INVENTION

The use of image data, generally available in digital form, of a patient which were obtained prior to surgery, e.g. x-ray or computed tomography or magnetic resonance imaging recordings for planning and performing invasive surgical interventions, is known per se. Such methods provide "internal views" of organs or body parts. In some methods, these image data are also created or updated during the operation in order to visualize possible changes in the recorded object, e.g. the operation progress or reactions of the body to the surgical intervention, which are not detectable, or can only be detected badly, by film cameras or video cameras. Three-dimensional models of one or more body parts and/or organs can be calculated from image data obtained by tomography.

Moreover, it is conventional to record optical recordings such as photographs or video images of the patient intraoperatively, e.g. using an endoscope, and to display these on a monitor together with the tomographic image data created prior to surgery, respectively as an individual image or in a superposed manner. In this manner, it is possible, for example, to make tissue to be removed or nerve tracts or vessels, which are situated in the operation region and potentially endangered by the surgical intervention, more visible to the surgeon. This display of the image data allows the surgeon to use the medical devices used during the operation as efficiently as possible and with minimal adverse effects on the surrounding tissue of the patient.

Image data obtained by computed tomography (denoted tomographic image data below) or image data obtained by x-ray technology allow the visualization of regions in the human body which would require an invasive method for the creation of image data obtained by photography or video technology (denoted as F/V image data below). Instead, tomographic image data are disadvantageous in relation to F/V image data in that they generally do not depict the recorded regions true to scale but rather in a distorted manner. The distortion of the tomographic image data is due to the system and is not subject to predictable laws, according to which it could be corrected by predetermined correction algorithms. Inclusion of tomographic image data in a system for operation planning and/or intraoperative navigation, such as e.g. a position detection system, therefore requires rectification of the tomographic image data which is as error-free as possible in order to achieve the desired accuracy.

Known rectification methods compare the distorted tomographic image data with corresponding F/V image data which image the same region, preferably from the same perspective, and carry out rectification of the tomographic image data on the basis of the established deviations of the tomographic image data from the F/V image data. Subsequently, the image data for example can be depicted on a display in a superposed manner.

Such known methods for rectifying tomographic image data are disadvantageous in that they often produce erroneous results. A reason for this is that the same perspective cannot be obtained exactly when creating the tomographic image data and F/V image data, and hence rectification is carried out on the basis of F/V image data with a different perspective. Furthermore, the different image data are often created at different times, and so e.g. acute swelling, bruising, etc. can lead to errors when rectifying the tomographic image data.

SUMMARY OF THE INVENTION

The invention is based on the object of specifying a more reliable method for including tomographic image data in a system for operation planning or for intraoperative navigation. The invention is likewise based on the object of providing a reference body, an electromagnetic field generator and a medical system, which are respectively suitable for use in such a method.

According to the invention, the object is achieved by a method for including image data obtained by computed tomography and/or x-ray-technology in a system for operation planning and/or for intraoperative navigation, comprising the following steps:

recording tomographic image data or image data obtained by x-ray technology of at least one defined body region of the patient by means of at least one first recording device suitable therefor, wherein a first reference body with at least one surface is arranged at the patient and also recorded by the first recording device;

comparing the recorded image data representing the first reference body with known geometric data of the first reference body for obtaining distortion information, rectifying the recorded image data by a computer unit on the basis of the distortion information in order to obtain rectified image data;

superposing the rectified image data with further image data of the same body region of the patient in order to obtain superposed image data; and depicting the superposed image data on a display.

The method includes the concept of making a computed tomography image prior to the operation and making intraoperative x-ray images (fluoroscopy images) using a C-arm. As a result of the body with a known geometry, the x-ray images (fluoroscopy images) recorded intraoperatively can be rectified and therefore compared with x-ray images which were generated virtually from the recordings prior to surgery, for example by a computed tomography scanner. This is advantageous in that a medical practitioner can orient himself during operation planning and when carrying out the operation using x-ray images, to be precise using both x-ray images recorded prior to surgery and x-ray images recorded intraoperatively. Instead of image data obtained by x-ray technology, it is also possible for image data to be recorded using a different imaging method, e.g. an ultrasound-based method. Likewise, the tomographic image data can be obtained by means of a computed tomography scanner, a magnetic resonance imaging scanner, an ultrasonic imaging scanner or the like.

The geometric data of the first reference body are preferably available as image data which depict the actual geometry of the first reference body in a non-distorted manner.

Preferably, the further image data of the same body region of the patient comprise the geometric data of the first reference body as image data.

Furthermore, it is preferable if the first reference body has the same position in relation to the recording device and/or patient when recording the further image data as when recording the tomographic image data so as not to have to take into account different positions when rectifying the image data It is also advantageous if the first reference body has the same distance from the recording device when recording the further image data as when recording the tomographic image data such that, where possible, no different distortions occur.

It is also advantageous if the first reference body is aligned in such a way when creating the tomographic image data that the largest possible part of the surface of the first reference body faces the recording device in order thus to be able to record image data of the reference body which are as significant as possible.

Preferably, the first reference body is arranged on a body position of the patient such that the body position and the first reference body can be detected with a recording that is as detailed as possible.

The further image data of the same body region of the patient can be created by a second recording device, preferably an x-ray device, and can comprise an x-ray image or fluoroscopy images.

Preferably, the reference body has localizers, such as e.g. sensor coils or optical localizers. This renders it possible to compare not only the recorded image data with known geometric data by way of rectification, but moreover also the reference field for intraoperative navigation. In the case of electromagnetic navigation known per se, this can be an alternating field generated by a field generator, which alternating field is detected by the sensor coils. Such a comparison of the recorded image data with the known geometric data and the reference field for intraoperative navigation enables a registration, which can be carried out not only prior to surgery but also intraoperatively.

The first reference body is preferably ring-shaped or circular and/or has ring-shaped and/or circular regions and/or elements.

Preferably, the further image data are recorded intraoperatively and are therefore very current.

The display preferably comprises a monitor.

The defined body region of the patient preferably comprises the vertebral column, i.e. the method is particularly advantageous for assisting examinations or treatments in the region of the vertebral column.

At least some of the tomographic image data can be recorded prior to an examination or operation, e.g. in a tomography scanner, for example a magnetic resonance imaging scanner, which would otherwise impede the examination or operation.

Particularly preferably, a second or further reference body is arranged at an operation site in the body of the patient, wherein the operation region is arranged in the defined body region of the patient. The first reference body and the second reference body are registered in a navigation system for planning and performing operations, wherein position data of the first reference body and of the second reference body are determined relative to a reference point by the navigation system. For the registration, it is advantageous if the first reference body and the second reference body have localizers, such as e.g. sensor coils or optical localizers. The use of sensor coils in such navigation systems is known per se. The tomographic image data and further image data can be depicted on the display in a superposed manner by means of the determined position data of the first reference body and of the second reference body in the navigation system. As a result, exact navigation with the help of intraoperatively obtained and rectified x-ray images is made possible. The accuracy of the superposition of the image data is optimized by registering the first reference body and the second reference body in a navigation system.

The use of two reference bodies, of which a first is the body with a known geometry and the second is a relatively small local localizer at the operation site, in combination renders it possible to obtain spatial information intraoperatively and superpose this into x-ray images generated intraoperatively.

Two of the reference bodies can also be bodies with a known geometry. By way of example, this renders it possible to obtain spatial information from e.g. fluoroscopy images, obtained by x-ray technology, particularly if a plurality of two-dimensional images without depth information (e.g. images obtained by x-ray technology) were recorded from different perspectives and are put into relationship with one another.

It is advantageous if the first reference body and/or the second reference body are detected in terms of position by means of an electromagnetic and/or optical position detection system. Preferably, the position detection is carried out at the same time as recording the image data and/or at the same time as recording the further image data.

In principle, both electromagnetic and optical position detection systems are known from the prior art. By way of example, electromagnetic position detection systems which comprise a field generator are known. The field generator generates a—generally alternating—alternating electric field in an operation region. Localization elements with coils are arranged on a medical instrument to be navigated in this operation region. The alternating electromagnetic field induces characteristic currents in these coils depending on the alignment of the respective coil in relation to the alternating electromagnetic field, from which currents the position information of the coils is determinable.

The first reference body and/or the second reference body can have a sensor coil as localizer and/or optical localizers, which is preferably fastened to the reference body or integrated into the latter. Preferably, the location of the reference body in relation to a localizer is known. The first reference body and/or the second reference body can be embodied in a manner attachable to and/or arrangeable on the patient and thus serve as patient localizer and/or patient reference for a position detection and/or navigation.

Preferably, a first reference body is provided to be arranged on a patient and to be removed again once registration has taken place. Preferably, a second reference body is provided to be arranged on a patient and to remain there at least temporarily after registration has taken place. A first and second reference body can be arranged on the patient simultaneously such that the relative position thereof in relation to one another can also be recorded by an image recording and/or determined by a position detection system.

Additionally or alternatively, at least some of the image data obtained by tomography or x-ray technology can be recorded during an operation (intraoperatively) and are therefore respectively very current. What lends itself particularly in this case is to record image data intraoperatively by means of a compact x-ray device such as e.g. a C-arm. Often, such image data recorded intraoperatively are fluoroscopy images without depth information and do not contain tomography images. Nevertheless, spatial information can then be obtained with the aid of one or more reference bodies having a known geometry. The latter applies in particular—but not only—if e.g. image data with spatial information, e.g. tomography images such as computed tomography images or magnetic resonance imaging images, obtained prior to surgery are also available, which are linked intraoperatively to image data obtained intraoperatively.

In respect of the medical system, the object is achieved by a medical system for operation, planning and/or intraoperative navigation, which comprises at least one computer unit, at least one first recording unit for recording tomographic image data of a body region of a patient, at least one second recording unit for recording further image data of the same body region of the patient and a first reference body, wherein the medical system is embodied to carry out a method of the type described above.

The reference body can be partly radiotransparent. Preferably, the reference body has radiopaque components, in particular radiopaque reference marks, wherein, preferably, the geometric position of the reference marks in relation to one another is known and fixed on the reference body. In this manner, there can be a prescribed comparison and rectification of recorded image data on the basis of the geometric position of the reference marks in relation to one another. Alternatively or additionally, a comparison and rectification of recorded image data can take place on the basis of the inherent geometry of the reference body.

Preferably, the reference marks have a planar embodiment and are arranged on the reference body in such a way that at least two, preferably at least 3 reference marks extend in a planar manner in a common plane.

A reference mark is preferably ring-shaped or circular and/or has ring-shaped and/or circular regions and/or elements.

The object in respect of the electromagnetic field generator is achieved by an electromagnetic field generator which has or forms a predetermined reference body. It was found to be advantageous if the reference body and/or the reference marks arranged on the reference body are arranged in a fixed position in respect of the electromagnetic field generator, in particular in respect of a field-generating element of the field generator. Preferably, the geometric location of the reference marks in relation to one another is known and fixed on the reference body.

The field generator and/or the field-generating element of the field generator can have a frame-shaped embodiment, in particular in such a way that the frame spans a window which—apart from radiopaque reference markers to be arranged in the window—is radiotransparent. The radiotransparent window can be formed by a planar radiotransparent reference body, on which radiopaque reference bodies are arranged. Further preferably, a surface of the field generator has a planar embodiment in order to lie on an operating table when in operation. If a patient lies on the operating table during an operation, the field generator is preferably arranged between patient and operating table. The field generator can have cushioning elements in order to avoid pressure points on the body surface of the patient.

BRIEF DESCRIPTION OF THE DRAWINGS

The invention is now intended to be explained in more detail with the aid of the figures on the basis of various exemplary embodiments. In detail.

DETAILED DESCRIPTION

Figure 1:
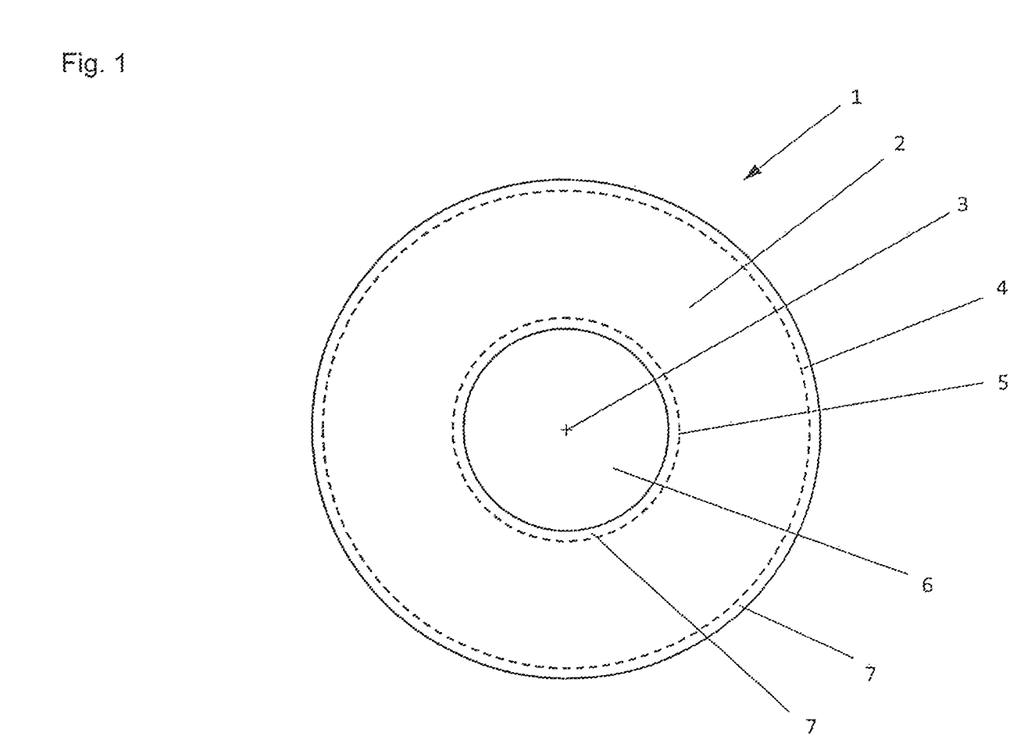
FIG. 1 shows a schematic top view of a first embodiment of a first reference body according to the invention.

The first embodiment of a first reference body 1 according to the invention, schematically depicted in FIG. 1, comprises a ring-shaped main body 2, depicted using dashed lines, with a center point 3, an outer circumference 4 and a smaller inner circumference 5. A circular through-hole 6 through the main body 2 is delimited by the inner circumference 5, which through-hole is concentric with the main body 2. The main body 2 is preferably formed from a material which exhibits poor transmissivity of x-ray beams. In particular, metals, such as e.g. lead, are suitable to this end. It is not possible to identify in this view that the two surfaces of the main body 2 have a flat embodiment. In alternative embodiments, one or both surfaces can also have a convex arching, which extends radially toward the center 3.

The main body 2 is completely encapsulated by a cover layer 7 made of material that differs from the material of the main body 2. In this first exemplary embodiment, the cover layer 7 is arranged exactly along the form of the main body 2. Preferably, the cover layer 7 exhibits a significantly better transmissivity of x-ray beams than the main body 2. Polymers, in particular, are suitable as material for the cover layer 7. The cover layer 7 is optional and offers e.g. hygienic advantages. Furthermore, a suitable cover layer 7 can also ensure the dimensional stability of the first reference body 1. The latter is important, particularly when the main body 2 is made from a very ductile material such as e.g. lead. A smooth surface and great brittleness of the cover layer 7 are particularly advantageous. Here, the cover layer should have such brittleness that a strong deformation of the first reference body 1, which extends beyond elastic deformability, causes at least local breakage of the cover layer 6. Therefore, a broken cover layer 6 serves as an indicator for a deformed first reference body 1, which as such should no longer be used.

Figure 2:
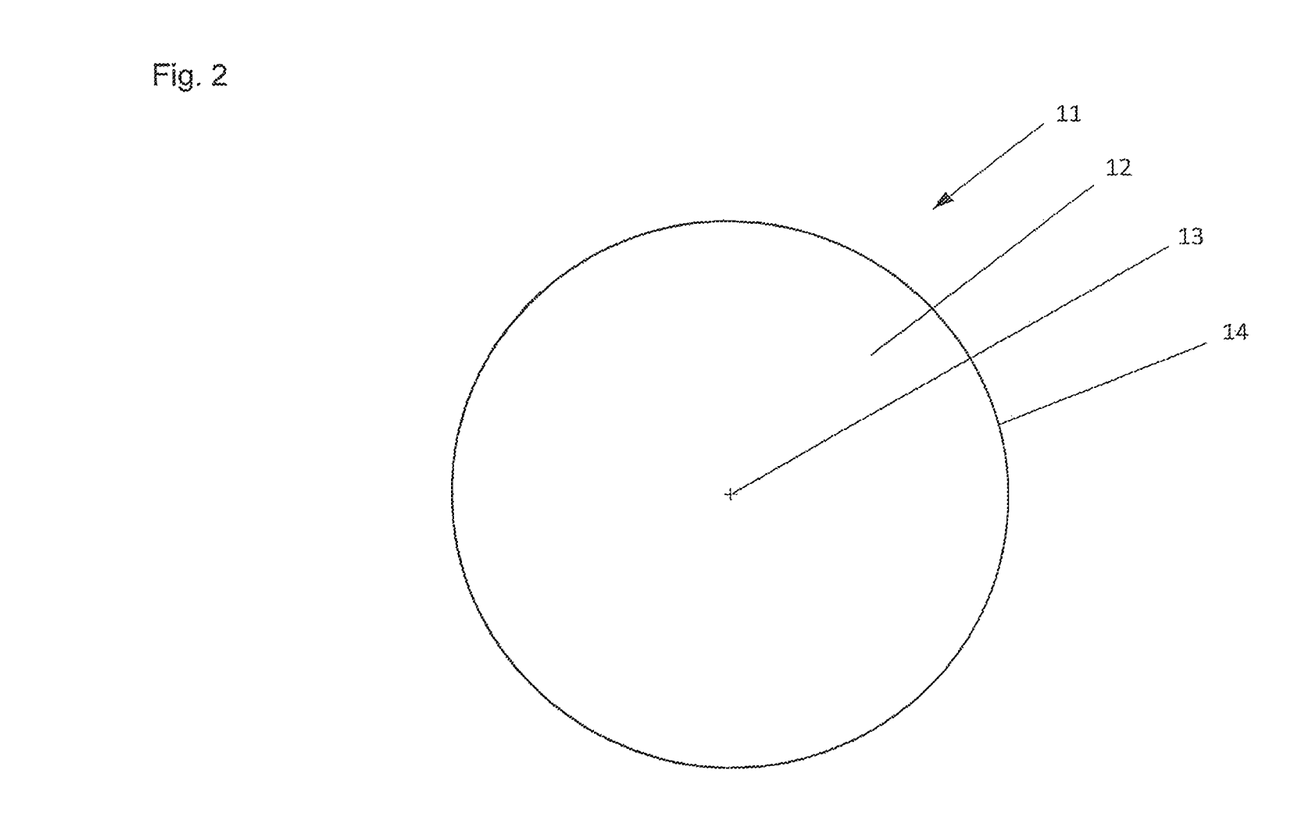
FIG. 2 shows a schematic top view of a second embodiment of a first reference body according to the invention.

The second embodiment of a first reference body 11 according to the invention, depicted in FIG. 2, has a circular main body 12 with a center point 13 and an external circumference 14. There is no cover layer in the imaged second exemplary embodiment; however, it can be added when necessary.

Figure 3:
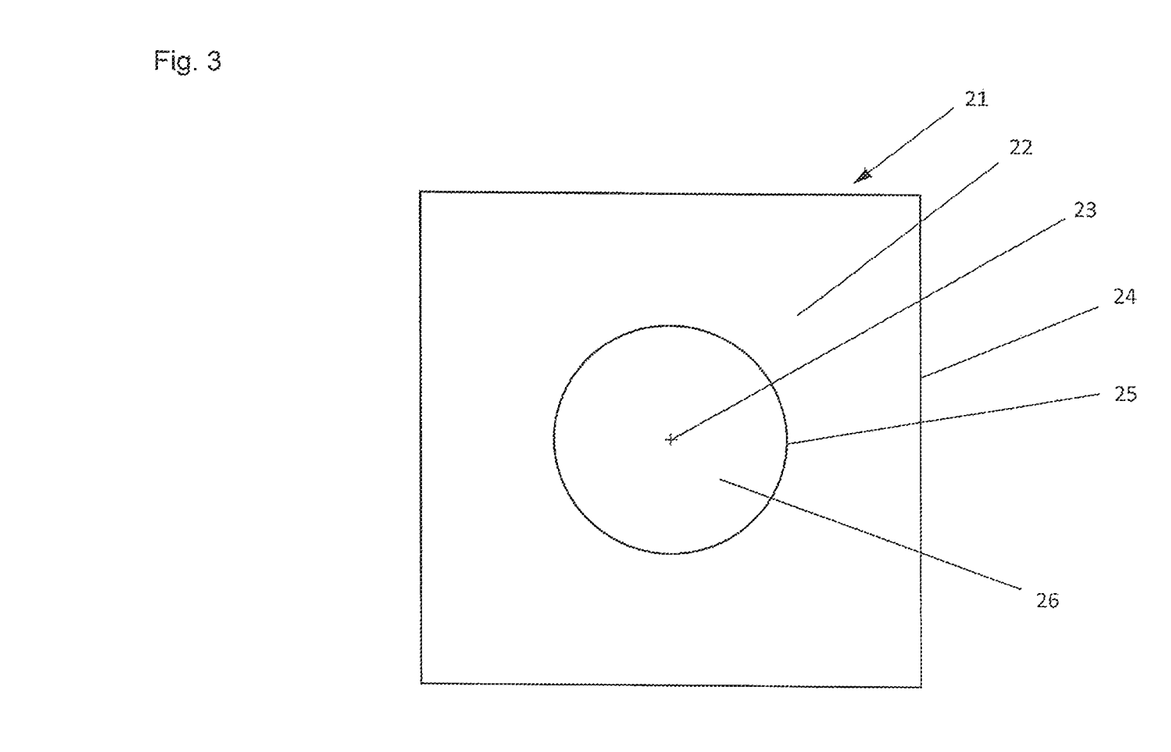
FIG. 3 shows a schematic top view of a third embodiment of a first reference body according to the invention.

FIG. 3 shows a third embodiment of a first reference body 21 according to the invention. The first reference body 21 has a square main body 22 with a center point 23, an external circumference 24 and a circular through-hole 26, which is concentric with the main body 22. The through-hole 26 is delimited toward the outside in the radial direction by way of an internal circumference 25 of the main body 22.

In the case where the main body 2, 12, 22 has a sufficient solidity such that it does not permanently deform under intended usage conditions, the possible top layer 7 can be formed from an elastic material, for example in order to protect the main body 2, 12, 22 from external influences such as impacts. In particular, rubbery-elastic substances, silicones, etc. come into question here. Preferably, the cover layer can also be embodied as an elastic or rigid envelope, into which the main body 2, 12, 22 is insertable.

To the extent that the cover layer 7 has a significantly better transmissivity of x-ray beams than the main body 2, the cover layer 7 can also completely surround the main body 2, 12, 22 along with the through-holes 6, 26. Hence, substantially the main body 2, 12, 22 is identifiable on an x-ray recording of the first reference body 1, 11, 21.

Figure 4:
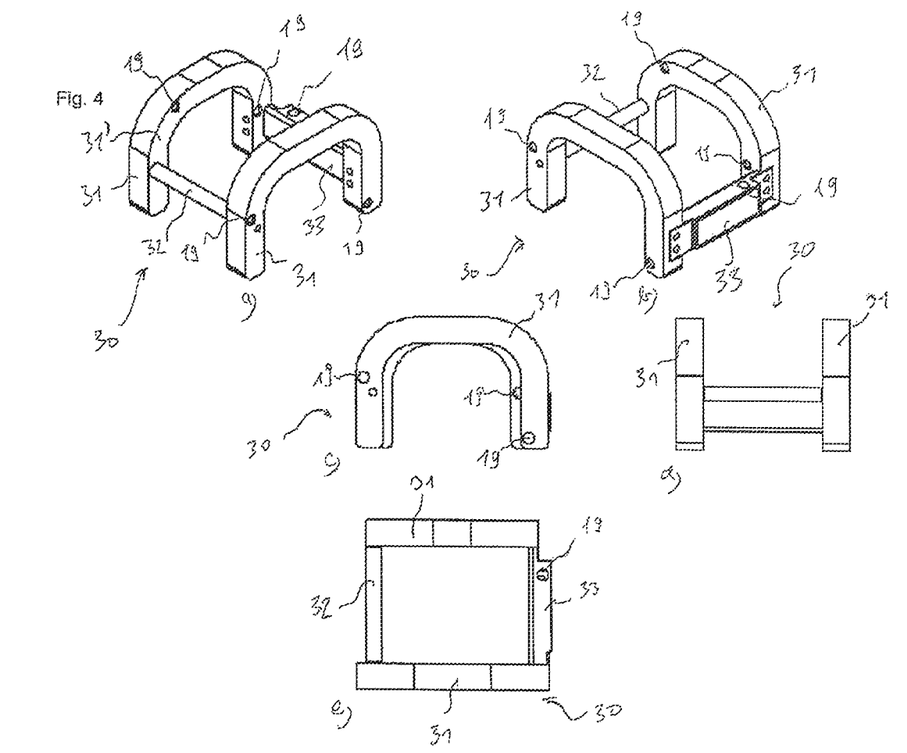
FIG. 4 shows a schematic illustration of a fourth embodiment of a first reference body according to the invention, which has reference marks.

A reference body 30 depicted in FIG. 4 is embodied as a cage and provided to be placed into an open operation region, e.g. an exposed vertebra. The reference body 30 has a plurality of reference marks 19, the geometric position of which in relation to one another is known and constant. The reference body 30 is made of a material which has a higher x-ray transmissivity than the reference marks 19. The reference body 30 has two u-shaped portions 31, which are arranged flush with one another and connected to one another by way of two webs 32, 33. Two Planar reference marks 19 are arranged on a surface 31' of the reference body 30 in such a way that they extend in a planar fashion in a common plane, namely the surface 31'. The sub-figures a) to e) respectively show different views of the same reference body 30.

Figure 5:
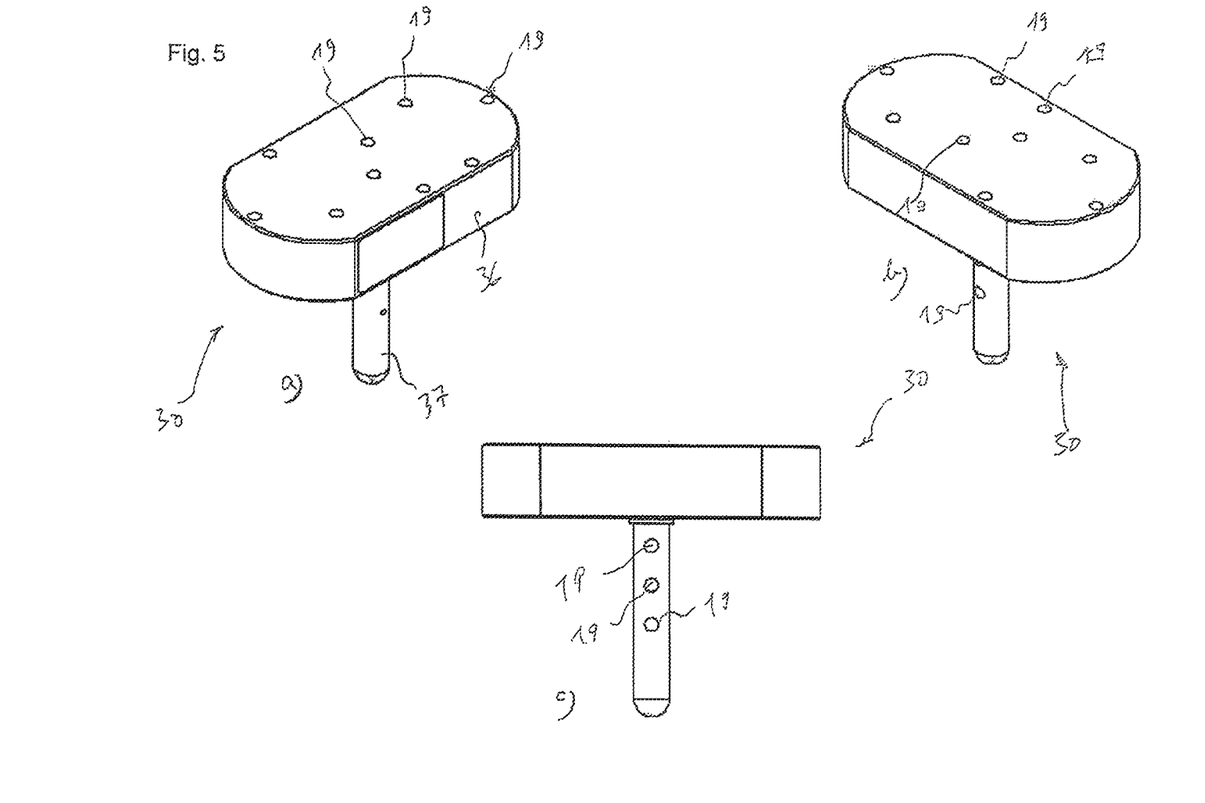
FIG. 5 shows a schematic illustration of a fifth embodiment of a first reference body according to the invention, which has reference marks.

An alternative reference body 30, depicted in FIG. 5, has a mushroom-shaped embodiment and is provided to be placed into a surgical skin opening which, for example, was opened by means of a trocar within the scope of a minimally invasive intervention. The reference body 30 has a flat cap 36, to which is attached centrally a pin 37. The reference body 30 has a plurality of reference marks 19 both on the cap 36 and on the pin 37, the geometric location of which reference marks in relation to one another is known and constant. The reference body 30 is made of a material which has a higher x-ray transmissivity than the reference marks 19. The sub-figures a) to c) respectively show different views of the same reference body 30.

Figure 6:
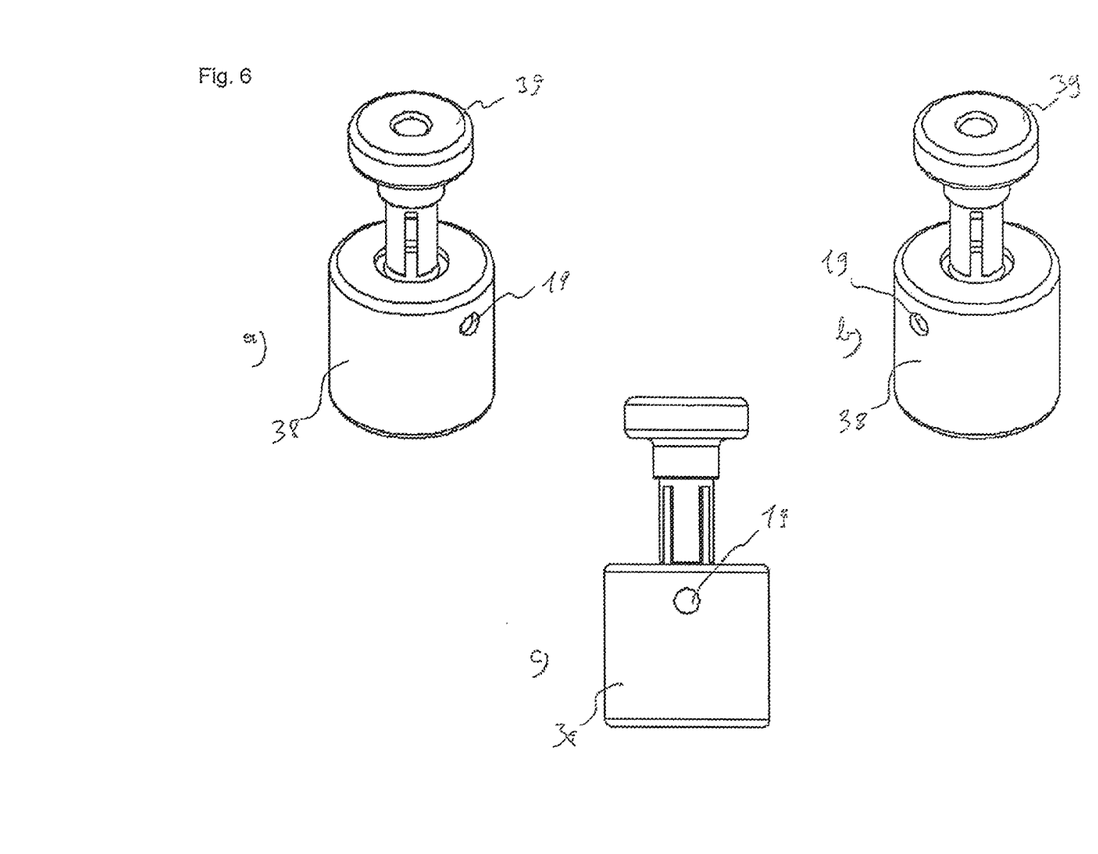
FIG. 6 shows a schematic illustration of a first embodiment of a second reference body according to the invention, which has reference marks.

Another alternative reference body 30, depicted in FIG. 6, has a sleeve-shaped embodiment and is provided, for example, to be drawn onto a surgical wire, e.g. a Kirschner wire to be fastened to the bone, and affixed thereon. To this end, the reference body 30 has an outer sleeve 38 and an insertable fixing sleeve 39. On the outer sleeve 38, the reference body 30 has a plurality of reference marks 19, the geometric position of which in relation to one another is known and constant. The reference marks 19 are arranged uniformly in the circumferential direction on the outer sleeve 38. The reference body 30 is made of a material which has a higher x-ray transmissivity than the reference marks 19. The sub-figures a) to c) respectively show different views of the same reference body 30.

Figure 7:
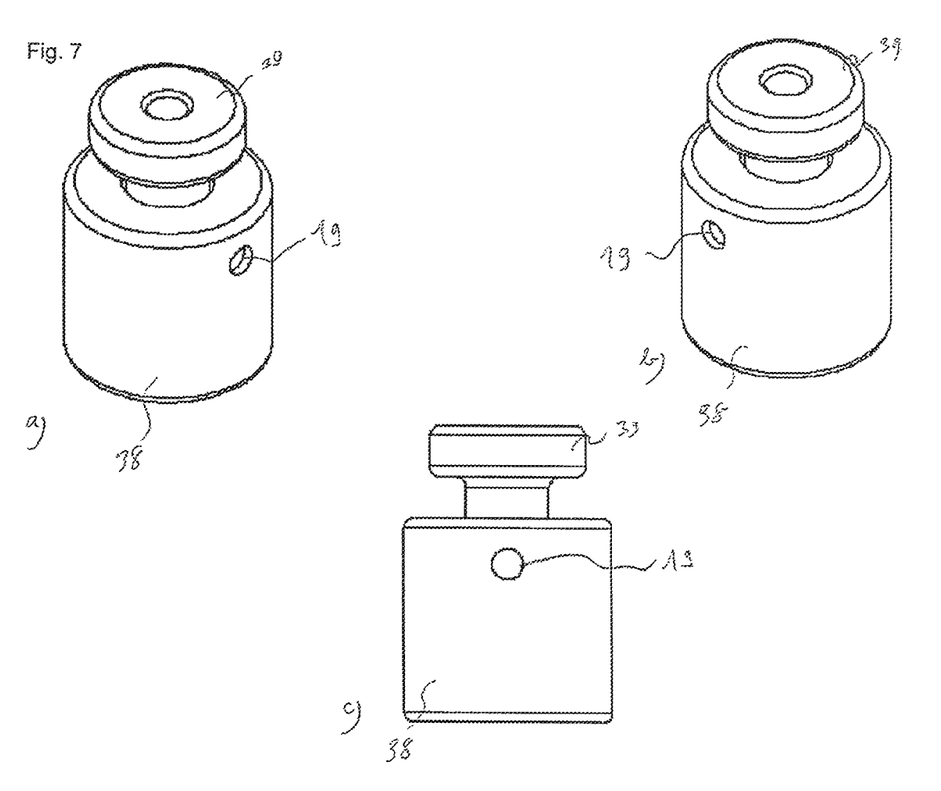
FIG. 7 shows a further schematic illustration of a second reference body from FIG. 6.

FIG. 7 show the reference body 30 from FIG. 6 in the fixed position, i.e. the reference body is affixed to a surgical wire (not shown here). To this end, the fixing sleeve 39 is pressed into the outer sleeve 38. The sub-figures a) to c) respectively show different views of the same reference body 30.

Figure 8:
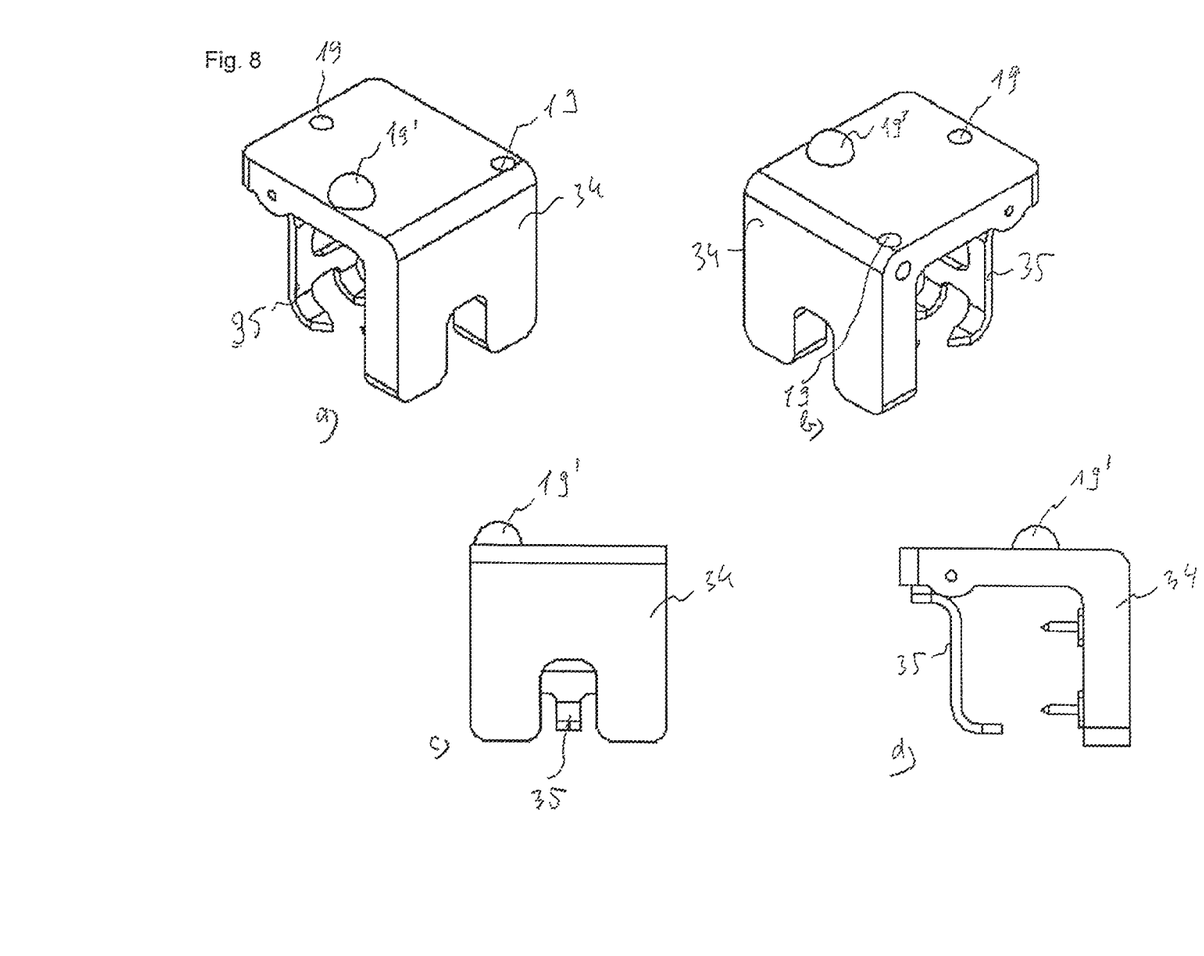
FIG. 8 shows a schematic illustration of a second embodiment of a second reference body according to the invention, which has reference marks.

A further alternative reference body 30, depicted in FIG. 8, has an embodiment in the shape of a clamp and is provided, for example, to be affixed to a vertebra. To this end, the reference body 30 has an angular main bracket 34, on which a clamping bracket 35 is attached in a pivotable manner. The reference body 30 has a plurality of reference marks 19, 19', the geometric position of which in relation to one another is known and constant. In the present case, the reference marks. 19, 19' are only arranged on a surface of the angular main bracket 34 and have different dimensions. The reference body 30 is made of a material which has a higher x-ray transmissivity than the reference marks 19. The sub-figures a) to d) respectively show different views of the same reference body 30.

Figure 9:
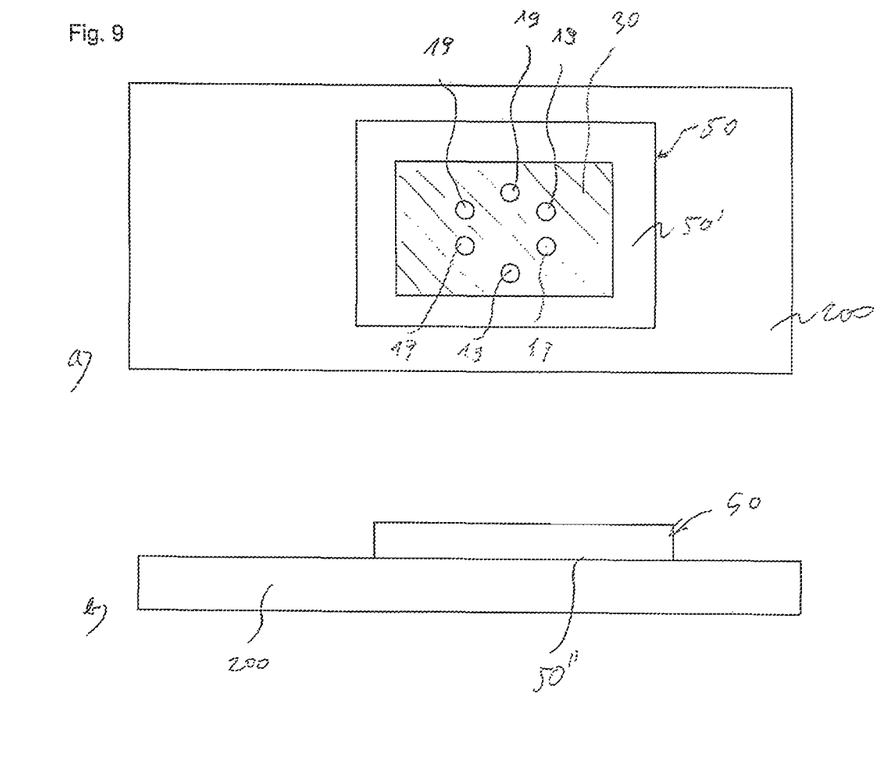
FIG. 9 shows a schematic illustration of an embodiment of a field generator according to the invention.

FIG. 9a) shows a top view of an operating table 200, with a field generator 50 according to the invention lying on said operating table 200. The field generator 50 and the (integrated and therefore not shown) field-generating element of the field generator 50 have a frame-shaped embodiment. The frame 50' of the field generator 50 spans a window (shaded area), which is radiotransparent. The radiotransparent window is formed by a planar radiotransparent reference body 30 in the present case. Arranged on the radiotransparent reference body 30 are reference marks 19, which are respectively arranged with a fixed position in relation to the field generator 50 and in relation to the integrated, and therefore not shown, field-generating element. The geometric position of the radiopaque reference marks 19 in relation to one another is known and constant.

As can be seen from the side view of FIG. 9b), the field generator 50 is embodied with a planar surface 50" and lies on the operating table 200.

Figure 10:
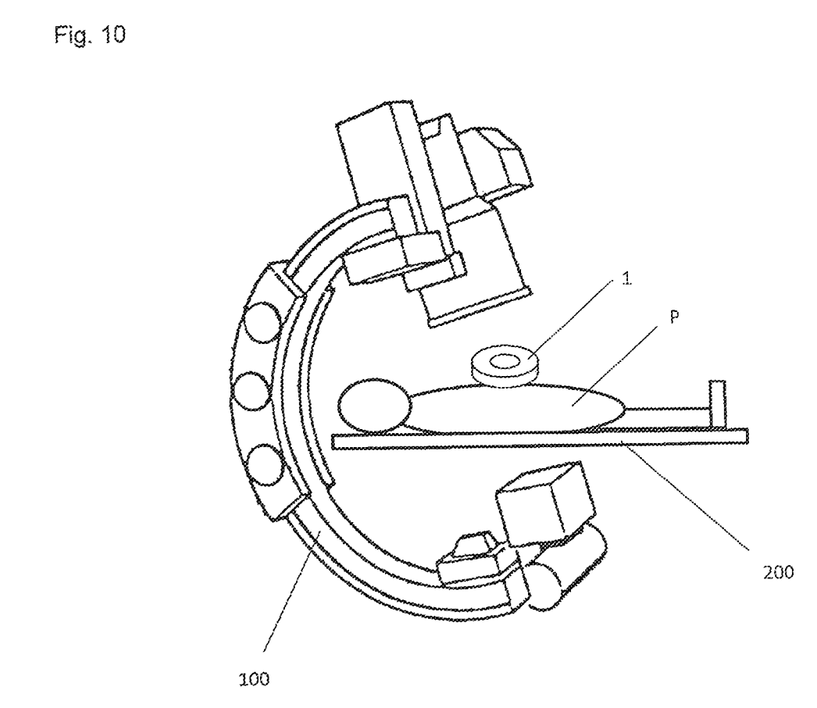
FIG. 10 shows a schematic illustration of an arrangement for intraoperative image recording and FIG. 11 shows a schematic illustration of a method according to the invention for including image data of a patient in a system for operation planning and/or intraoperative navigation.

An arrangement for intraoperative image recording is shown in FIG. 10. A first reference body 1, for example the one described with reference to FIG. 1, is arranged abdominally on a patient P lying on an operating table 200. The patient P and the reference body 1 are positioned in a C-arm in such a way that the image data obtained by x-ray technology comprise both a defined body region of the patient P, the abdomen in the present case, and the reference body 1 arranged there.

Figure 11:
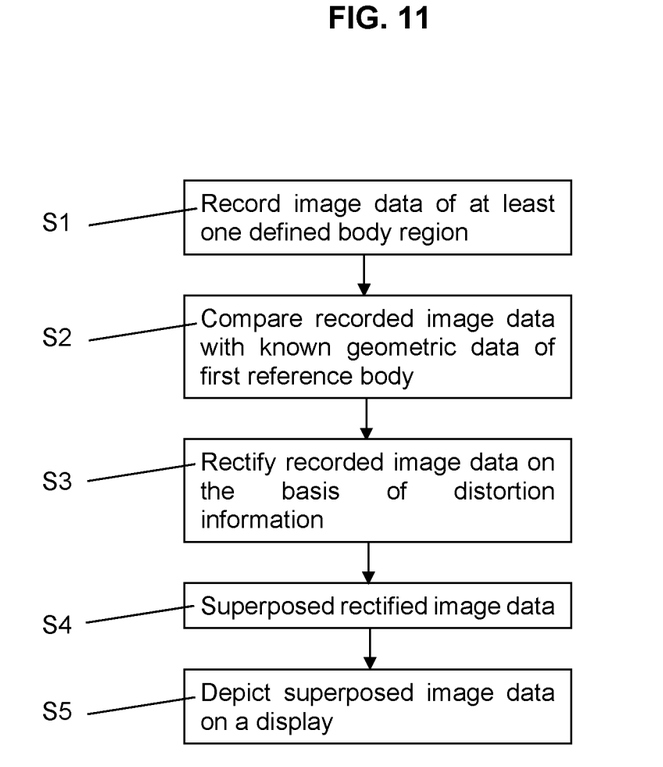

In a method according to the invention for including image data of a patient in a system for operation planning and/or intraoperative navigation in FIG. 11, tomographic image data or image data obtained by x-ray technology of at least one defined body region of the patient are recorded in a first step S1 by means of at least one first recording device suitable therefor, wherein a first reference body with at least one surface is arranged at the patient and also recorded by the first recording device.

In a second step S2, the recorded image data representing the first reference body are compared with known geometric data of the first reference body for obtaining distortion information.

In a third step S3, recorded image data are rectified by a computer unit on the basis of the distortion information in order to obtain rectified image data.

In a fourth step S4, the rectified image data are superposed on further image data of the same body region of the patient in order to obtain superposed image data.

In a fifth step S5, the superposed image data are depicted on a display.

LIST OF REFERENCE SIGNS 1, 11, 21, 30 Reference body
2, 12, 22 Main body
3, 13, 23 Center Point
4, 14, 24 External circumference
5, 25 Internal circumference
6, 26 Circular through-hole
7 Cover layer
19, 19' Reference mark
31 U-shaped portion
31' Surface of the reference body
32, 33 Web
34 Main bracket
35 Clamping bracket
36 Cap
37 Pin
38 Outer sleeve
39 Fixing sleeve
50 Field generator
50' Frame of the field generator
50" Plane surface of the field generator
100 C-arm
200 Operating table
P Patient
S1, S2, S3, S4, S5 Method steps

The invention claimed is:

1. A method for including image data of a patient in a system for operation planning or intraoperative navigation, comprising the following steps:
providing a first reference body, wherein the first reference body has a known three-dimensional geometry;
providing available geometric data representing said first reference body in its known three-dimensional geometry in a non-distorted manner;
arranging the provided first reference body with at least one body surface on a patient;
recording tomographic image data or image data obtained by X-ray technology of at least one defined body region of the patient together with the first reference body arranged on the patient by at least one first recording device suitable therefor,
comparing the recorded image data representing the first reference body hi a distorted manner with said known geometric data representing the first reference body in a non-distorted manner for obtaining distortion information,
rectifying said recorded tomographic image data or image data obtained by X-ray technology of at least one defined body region of the patient by a computer unit on the basis of the obtained distortion information in order to obtain rectified image data;
superposing the rectified image data with further image data of the same body region of the patient in order to obtain superposed image data; and
depicting the superposed image data on a display.

2. The method as claimed in claim 1,
wherein the geometric data of the first reference body are image data which image the actual geometry of the first reference body in a non-distorted manner.

3. The method as claimed in claim 1,
wherein the further image data of the same body region of the patient comprise the geometric data of the first reference body as image data.

4. The method as claimed in claim 3,
wherein the first reference body has the same position in relation to the recording device or patient when recording the further image data as when recording the tomographic image data.

5. The method as claimed in claim 3,
wherein the first reference body has the same distance from the recording device when recording the further image data as when recording the tomographic image data.

6. The method as claimed in claim 1,
wherein the first reference body is aligned in such a way when recording the tomographic image data that the largest possible part of the surface of the first reference body faces the recording device.

7. The method as claimed in claim 1,
wherein the first reference body is arranged on a body position of the patient.

8. The method as claimed in claim 1,
wherein the further image data of the same body region of the patient are recorded by a second recording device, wherein the second recording device is an X-ray device and the further image data comprise fluoroscopy images.

9. The method as claimed in claim 1,
wherein the first reference body is ring-shaped or circular or has ring-shaped or circular regions or elements.

10. The method as claimed in claim 1,
wherein the further image data are recorded intraoperatively.

11. The method as claimed in claim 1,
wherein the defined body region of the patient comprises the vertebral column.

12. The method as claimed in claim 1,
wherein a second reference body is arranged at an operation site in the body of the patient, wherein the operation region is arranged in the defined body region of the patient, wherein the first reference body and the second reference body are registered in a navigation system for planning and performing operations, wherein position data of the first reference body and of the second reference body are determined relative to a reference point by the navigation system, wherein the tomographic image data and further image data are depicted in a superposed manner on the display by the position data of the first reference body and of the second reference body in the navigation system.

13. The method as claimed in claim 1,
wherein at least some of the tomographic image data are recorded during an examination or operation.

14. The method as claimed in claim 1, wherein the first reference body or the second reference body are detected in terms of position by an electromagnetic or optical position detection system.

15. The method as claimed in claim 14, wherein the position detection is carried out at the same time as recording the image data or at the same time as recording the further image data.

16. The method as claimed in claim 1, wherein the reference body has reference marks, the geometric position of which in relation to one another is known and constant.

17. The method as claimed in claim 16, wherein the reference body is arranged at a field generator, wherein the field generator or the field-generating element of the field generator have a frame-shaped embodiment, in such a way that the frame spans a window which—apart from radiopaque reference marks to be arranged in the window—is radiotransparent.

18. A medical system for operation planning or intraoperative navigation, comprising a computer unit, at least one first recording unit for recording tomographic image data of a body region of a patient, at least one second recording unit for recording further image data of the same body region of the patient and a reference body, wherein the medical system is embodied to carry out a method as claimed in claim 1.

* * * * *

UNITED STATES PATENT AND TRADEMARK OFFICE
CERTIFICATE OF CORRECTION

PATENT NO. : 10,362,966 B2  
APPLICATION NO. : 14/890480  
DATED : July 30, 2019  
INVENTOR(S) : Timo Kruger et al.

Page 1 of 1

It is certified that error appears in the above-identified patent and that said Letters Patent is hereby corrected as shown below:

In the Claims

In Column 9, Line 55, Claim 1, Line 17, "hi" should be deleted and -- in -- inserted therefor.

Signed and Sealed this  
Tenth Day of November, 2020

Andrei Iancu  
*Director of the United States Patent and Trademark Office*